United States Patent
Wlassics et al.

(10) Patent No.: US 7,358,405 B2
(45) Date of Patent: *Apr. 15, 2008

(54) DEHALOGENATION PROCESS

(75) Inventors: Ivan Wlassics, Genoa (IT); Vito Tortelli, Milan (IT)

(73) Assignee: Solvay Solexis SpA, Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 11/416,129

(22) Filed: May 3, 2006

(65) Prior Publication Data

US 2006/0252966 A1 Nov. 9, 2006

(30) Foreign Application Priority Data

May 5, 2005 (IT) .......................... MI2005A0818

(51) Int. Cl.
*C07C 17/00* (2006.01)
*C07C 17/25* (2006.01)
*C07C 19/08* (2006.01)

(52) U.S. Cl. .................. 570/156; 570/128; 570/155; 570/158

(58) Field of Classification Search ............. 570/226, 570/227, 228, 230

See application file for complete search history.

(56) References Cited

FOREIGN PATENT DOCUMENTS

EP     0 349 963 A     1/1990
EP     1 247 791 A1     10/2002

OTHER PUBLICATIONS

Cohen et al., Journal of the American Chemical Society (1950), 72, 3952-3.*
Spraul et al., Journal of the American Chemical Society (2006), 128(21), 7055-7064.*
Encyclopedia Houben Weyl, vol. E10 B2, pp. 125-161.
Smith et al., "Perfluorocyclobutane Aromatic Polyethers. Synthesis and Characterization of New Siloxane-Containing Fluoropolymers"—Macromolecules, vol. 29, 1996, pp. 852-860.
Gorbunova et al., "Synthesis of Polyfluorinated Dienes"—Russian J. Org. Chem., 35(11), 1999, pp. 1557-1566.
Li et al., "Spontaneous Reactions of Potassium Phenoxide with Dibromoperfluoroalkanes-First Evidence for Bromophilic Attack on C-Br Bonds by the Phenoxide Ion"—Tetrahedr. Letters, 25(43), 1984, pp. 4937-4940.
Gang et al., "$Na_2S_2O_4/NaHCO_3$-system promoted addition-cyclization of per(poly)fluoroalkyl iodides or perhaloalkanes with 1,6-heptadienes"—J. Fluor. Chem., vol. 86, 1997, pp. 89-97.
Smith D.W. et al: "Perfluorocyclobutane Aromatic Polyethers. Synthesis and Characterization of New Siloxane-Containing Fluoropolymers" Macromolecules, vol. 29, No. 3, Jan. 29, 1996, pp. 852-860, XP000548540 ISSN: 0024-9297 p. 583, right-hand column, line 52-71.
"Houben-Weyl: Methods of Organic Chemistry, vol. E. 10B2" 1999, Georg Thieme Verlag, Stuttgart, XP002441628, p. 125-p. 161.
Smith D.W. et al.: "Anamalous crystallinity in a semi-fluorinated perfluorocyclobutyl (PFCB) polymer containing the hexafluoro-i-propylidene (6F) linkage" Polymer, vol. 45, No. 17, Aug. 5, 2004, pp. 5755-5760, XP004546859, ISSN: 0032-3861, left-hand column, line 1-25.

* cited by examiner

*Primary Examiner*—Karl Puttlitz
(74) *Attorney, Agent, or Firm*—Arent Fox, LLP.

(57) ABSTRACT

A process for obtaining vinyl compounds by dehalogenation of halofluorinated compounds with aromatic substituents, having formula:

$$T-Ar-(O)_y-CFX'-CF_2X'' \quad (I)$$

wherein:
X'=F, Cl, Br, I;
X"=Cl, Br, I;
y=0,1; when y=0 X'≠F;
T=H, —$(O)_y$—CFX'—$CF_2$X", wherein y, X' and X" are as above;
Ar is a monocyclic, bicyclic or tricyclic bivalent aromatic radical from 6 to 14 carbon atoms, optionally containing heteroatoms, or Ar is formed of two aromatic rings linked by a bivalent radical;
said process characterized in that the halofluorinated compounds are dehalogenated in the presence of a transition metal, by operating in a biphasic system of solvents immiscible among each other, formed of a (per)fluorinated solvent and a dipolar aprotic or protic solvent (co-solvent), wherein the ratio moles co-solvent/equivalents of the halofluorinated compound with aromatic substituents ranges from 0.5 to 10.

15 Claims, No Drawings

DEHALOGENATION PROCESS

The present invention relates to a process for obtaining fluorinated olefins containing aromatic groups, by dehalogenation of halofluorinated compounds, containing in the molecule aromatic groups and halogen atoms different from fluorine.

It is known in the prior art, see for example the Houben Weyl Encyclopedia, vol. E 10B2, pages 125-161, that the dehalogenation process of halofluorinated compounds, wherein the halogen is generally selected from chlorine and/or bromine, is carried out by using heterogeneous systems formed of one or more transition metals and of solvents which can be either hydrogenated protics, as alcohols, or hydrogenated ethers, as dioxane; or dipolar aprotics, as DMF. The transition metal used is selected for example from zinc, manganese, copper. Metal couples as Zn/Cu, Zn/Sn, Zn/Hg can also be used. It is also known that, in dehalogenation reactions, saturated and/or unsaturated fluorinated reduction by-products containing hydrogen can be formed, thus lowering the yield of the main reaction product. According to the above reference, see in particular page 127, it is possible to increase the yields, and therefore to reduce the amount of undesired hydrogenated compounds, by using dipolar aprotic solvents. It is known in the prior art that, by using in dehalogenation reactions dipolar aprotic solvents, as well as protic solvents, complexes are formed with the halogenated salt of the transition metal which forms in the reaction itself. For example, when zinc is used, the halogenated salt formed is the zinc chloride. From the industrial point of view the formation of the complex solvent-halogenated salt of the transition metal represents a drawback, as the recovery of the solvent becomes difficult. Besides, in the processes according to the prior art, it is important to avoid the prolonged contact between the dehalogenated reaction product and the solvent, since secondary reactions can take place in the reaction raw product with consequent detriment of the yields. One way to reduce some secondary reactions in the dehalogenation would be the removal, as quick as possible, of the dehalogenated compound formed in the reaction raw product. This operation can be carried out by distillation if the volatility of the dehalogenated product with respect to the solvent is high. In the case of starting products containing aromatic rings the boiling point is high, wherefore it is difficult to remove the product during the reaction.

This is also valid for the purification of the obtained dehalogenated compound, which can contain hydrogenated by-products having similar chemico-physical properties. Therefore the latter are hardly separated from the main product. For applications, as for example monomers, for example for preparing polymers for optical applications,. it is important from an industrial point of view to obtain dehalogenated compounds having the highest possible purity degree. Therefore the hydrogenated impurities in high amounts are hardly separable from the dehalogenated product. In other applications, for example in the pharmaceutical field, it is often required that the used components do not contain in high amounts by-products which could cause side reactions.

The need was felt to have available a dehalogenation method of halofluorinated compounds containing chlorine and/or bromine, to obtain vinyl products having an improved yield combined with improved selectivity in comparison with the dehalogenation processes of the prior art and with a substantial reduction of hydrogenated by-products.

The Applicant has surprisingly and unexpectedly found a process to solve the above technical problem.

An object of the present invention is a process for obtaining vinyl compounds with aromatic substituents, by dehalogenation of halofluorinated compounds with aromatic substituents having general formula:

$$T\text{-}Ar\text{—}(O)_y\text{—}CFX'\text{—}CF_2X'' \qquad (I)$$

wherein:

X'=F, Cl, Br, I;

X''=Cl, Br, I;

y is an integer 0, 1; when y=0 X'≠F;

T=H, —(O)$_y$—CFX'—CF$_2$X'', wherein y, X' and X'' are as above;

Ar is a monocyclic, bicyclic or tricyclic bivalent aromatic radical from 5 to 14 carbon atoms, optionally the ring containing one or more heteroatoms, or Ar is formed of two aromatic rings linked by a bivalent radical selected from the following:

(A)

(B)

(C)

said aromatic radical Ar optionally being subsituted with one or more substituents selected from the following:

Cl, F, Br, OH;

C$_1$-C$_8$ alkyl;

—COOH, or an acyl group —C(O)R, wherein R is H, or C$_1$-C$_8$ alkyl, C$_5$-C$_{14}$ aryl, C$_3$-C$_6$ cycloalkyl;

said process characterized in that the halofluorinated compounds are dehalogenated in the presence of a transition metal, by operating in a biphasic system of solvents immiscible among each other, formed of a (per)fluorinated solvent and a dipolar aprotic solvent (co-solvent), wherein the ratio moles of co-solvent/equivalents of the halofluorinated compound with aromatic substituents ranges from 0.5 to 10, preferably from 0.5 to 5, still more preferably from 1 to 3.

As said, the Ar ring can contain heteroatoms, preferably selected from O, S and N.

As co-solvent, alternatively to dipolar aprotic solvents, protic solvents can be used.

With equivalents of the halofluorinated compound are meant the moles of halofluorinated compound multiplied by the number of groups —CFX'—CF$_2$X'' present in the compound.

As said, the dehalogenation reaction can be applied to a wide range of halofluorinated products containing functional groups, provided that said functional groups are unable to react with the transition metals, and/or the co-solvent.

According to the present invention, with solvents immiscible among each other it is meant that the solvents form two distinct phases.

The compounds of formula (I) are obtainable with the process described in D. W. Smith et al., Macromolecules, vol. 29 (1996) pages 852-860; T. I. Gorbunova et al., Russian J. of Organic Chem., Vol. 35 (1999) 1557-1566; X. Li et al., Tetrahedr. Letters 45, 4937-4940 (1984), Z. Gang et al., J. Fluor. Chem. 86 (1997) 89-97.

Preferably in the compounds of formula (I) X'=F, X"=Br, y=1, Ar is formed of two aromatic rings linked by the bivalent radical (A), T=—(O)$_y$—CFX'—CF$_2$X", wherein y, X' and X" are as above.

In the process of the present invention one generally operates at temperatures between room temperature (20° C.) and 200° C., preferably between 50° C. and 150° C., with the proviso that the reaction temperature is lower than the boiling temperature of the (per)fluorinated solvent and of the co-solvent used.

Generally one operates under atmospheric pressure.

The transition metals usable in the process of the present invention are preferably selected from the following: zinc, manganese, copper. Alternatively, transition metal couples as for example Zn/Cu, Zn/Sn, Zn/Hg, can also be used.

As (per)fluorinated solvents, in the process of the present invention, liquid and inert compounds in the above temperature range can be used. Compounds or respective mixtures, selected from (per)fluorocarbons; (per)fluoroethers; (per)fluoropolyethers; perfluoroamines; hydrofluoroethers or hydropolyfluoroethers, can for example be used, the latter respectively known with the commercial names HFE® and H-Galden®. In hydrofluoroethers and in hydropolyfluoroethers the end groups of the fluorinated molecule are —H (H-Galden®), —OCH$_3$, —OC$_2$H$_5$, —OC$_3$H$_7$ (HFE®). H-Galden® is a product by Solvay Solexis, HFE® is a product by 3M.

Among perfluoroethers Galden® D-100 can for example be used, having a boiling point of about 100° C., formed of a mixture of 80% by moles of perfluoro-2-butylfuran and 20% by moles of perfluoro-2-propylpyran.

Among perfluoropolyethers, Galden® HT-110 having boiling point of 110° C. can for example be used.

The used co-solvent must be liquid and substantially inert under the reaction conditions. For example compounds selected from the following classes can be used: linear or branched C$_1$-C$_8$ alcohols; dipolar aprotic solvents as dimethylformamide, dimethylacetamide, dimethylsulphoxide, morpholine, acetonitrile; ethers as diglyme, tetraglyme, 1,4-dioxane and mixtures thereof.

The reaction is generally carried out under stirring, by adding the halofluorinated compound to a mixture, previously brought to the reaction temperature, formed of the (per)fluorinated solvent, co-solvent, the metal or transition metal couples.

The selectivity of the process of the invention is very high. The reaction times are generally lower than 8 hours.

The transition metal is used in an amount such that the ratio moles of transition metal/equivalents of halofluorinated compound is between 1 and 5, preferably between 1 and 3.

The process of the present invention can be carried out by using variable amounts of (per)fluorinated solvent, one preferably operates by using ratios by weight (per)fluorinated solvent : halofluorinated compound from 1:2 to 1:20, preferably from 1:3 to 1:5.

As said, with the process of the present invention it is possible to obtain dehalogenated compounds containing hydrogenated by-product amounts lower than those obtained by dehalogenating the same halofluorinated compounds by using the processes of the prior art.

The following Examples are for illustrative and not limitative purposes of the present invention.

EXAMPLES

Determination of the Purity of the Compound Obtained by Dehalogenation

The reaction products have been identified and quantified by quantitative $^{19}$F-NMR and $^1$H-NMR, quantitative gaschromatography and mass spectroscopy.

Example 1

Dehalogenation reaction (debromofluorination) of the compound having formula:

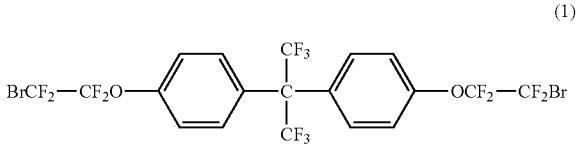

The compound of formula (1) has been synthesized according to D. W. Smith et al., Macromolecules, vol. 29 (1996) page 853.

An amount of D-100® (mixture of 80% by moles of perfluoro-2-butylfuran and 20% by moles of perfluoro-2-propylpyran) equal to twice the weight of the compound of formula (1), finely milled Zn in a molar amount equal to twice the moles of (1), and a molar amount of dimethylformamide (DMF) (hydrogenated co-solvent) equal to twice the moles of (1) are transferred in a 3-necked flask equipped with a dropping bottle, bubble condenser, thermometer and magnetic anchor. The mixture is left under stirring at a temperature of 100° C. for a zinc activation time -of 20 minutes. When this phase is over, the liquid compound (1) is dropped at a rate of 0.6 eq/hour. It is left at the reaction temperature and under stirring up to complete conversion of (1), that is for a time of 5 hours. The conversion is followed by periodically analyzing the raw product by $^{19}$F-NMR analysis, as above described.

At the end of the reaction, the reaction raw product is filtered from the residual Zn and from the Zn salts formed during the conversion of (1). The fluorinated solvent and the hydrogenated co-solvent are removed by distillation at reduced pressure. The selectivity of the desired product (2) is equal to 92%, with respect to the reaction by-products (3) and (4) having respectively the following formulas:

being in (4) Rf=—CF$_2$CF$_2$Br or —CF$_2$CF$_2$H; while for the by-products (3) and (4) it is globally equal to 8% (determined by quantitative $^{19}$F-NMR analysis).

The data obtained in the Example compared with those reported in literature by D. W. Smith et al., Macromolecules 29 (1996) 853, show a higher selectivity in the desired product (2), 92% vs 79%.

The invention claimed is:

1. A process for obtaining vinyl compounds of formula T-Ar—(O)$_y$—CF=CF$_2$ by dehalogenation of halofluorinated compounds having formula:

$$\text{T-Ar—(O)}_y\text{—CFX'—CF}_2\text{X''} \quad (I)$$

wherein:

X'=F, Cl, Br, I;

X''=Cl, Br, I;

y is an integer 0, 1; when y=0 X'≠F;

T=H, —(O)$_y$—CFX'—CF$_2$X'', wherein y, X' and X'' are as above;

Ar is a monocyclic, bicyclic or tricyclic bivalent aromatic radical from 5 to 14 carbon atoms, optionally the ring containing one or more heteroatoms, or Ar is formed of two aromatic rings linked by a bivalent radical selected from the following:

(A) —C(CF$_3$)(CF$_3$)—;

(B) —C(CH$_3$)(CH$_3$)—;

(C) —S(=O)(=O)—;

said aromatic radical Ar being substituted with at least one substituent selected from the following:

Cl F, Br, OH;

C$_1$-C$_8$ alkyl;

—COOH, or a —C(O)R acyl group, wherein R is H, or C$_1$-C$_8$ alkyl, C$_5$-C$_{14}$ aryl, C$_3$-C$_6$ cycloalkyl;

said process characterized in that the halofluorinated compounds are dehalogenated in the presence of a transition metal, by operating in a biphasic system of solvents immiscible among each other, formed of a (per)fluorinated solvent and a dipolar aprotic or protic solvent (co-solvent), wherein the moles ratio of co-solvent/equivalent of the halofluorinated compound with aromatic substituents ranges from 0.5 to 10.

2. A process according to claim 1, wherein the heteroatom in the Ar ring is selected from S, O or N.

3. A process according to claim 1, wherein in the compounds of formula (I) X'=F, X''=Br, y=1 and Ar is formed of two aromatic rings linked by the bivalent radical (A), T=—(O)$_y$—CFX'—CF$_2$X'', y, X' and X'' being as defined.

4. A process according to any one of claims 1 to 3, wherein the process is performed at a temperature in the range 20° C.-200° C.

5. A process according to claim 1, wherein transition metals selected among Zinc, manganese or copper are used.

6. A process according to claim 5, wherein transition metal couples preferably selected from Zn/Cu, Zn/Sn, Zn/Hg are used.

7. A process according to claim 1, wherein the (per)fluorinated solvents used are selected from (per)fluorocarbons; (per)fluoroethers; (per)fluoropolyethers; perfluoroamines; hydrofluoroethers or hydropolyfluoroethers, or mixtures thereof.

8. A process according to claim 7, wherein as perfluoroether a mixture formed of 80% by moles of perfluoro-2-butylfuran and 20% by moles of perfluoro-2-propylpyran is used.

9. A process according to claim 7, wherein a perfluoropolyether having boiling point 110° C. is used.

10. A process according to claim 1, wherein the co-solvent is selected from the following classes: linear or branched C$_1$-C$_8$ alcohols; dipolar aprotic solvents preferably selected from dimethylformamide, dimethylacetamide, dimethylsulphoxide, morpholine, acetonitrile; ethers preferably selected from diglyme, tetraglyme, 1,4-dioxane; and mixtures thereof.

11. A process according to claim 1, wherein the moles ratio of transition metal/equivalents of halofluorinated compound is between 1 and 5.

12. The process of claim 11, wherein the moles ratio of transition metal/equivalents of halofluorinated compound is between 1 and 3.

13. The process of claim 1, wherein the moles ratio of co-solvent/equivalent of the halofluorinated compound with aromatic substituents ranges from 0.5 to 5.

14. The process of claim 1, wherein the moles ratio of co-solvent/equivalent of the halofluorinated compound with aromatic substituents ranges from 1 to 3.

15. The process of any one of claims 1 to 3, wherein the process is performed at a temperature in the range 50° C.-150° C.

* * * * *